US00PP09336P

United States Patent [19]

Beckmann

[11] Patent Number: Plant 9,336

[45] Date of Patent: Oct. 17, 1995

[54] POINSETTIA PLANT NAMED 'BECKMANNS ALTROSA'

[76] Inventor: Kail-Rudolf Beckmann, Gaertnersiedlung 16, 24610 Goennebeck, Germany

[21] Appl. No.: 338,098

[22] Filed: Nov. 9, 1994

[51] Int. Cl.[6] ..... A01H 5/00

[52] U.S. Cl. ..... Plt./86.3

[58] Field of Search ..... Plt./86.3

[56] References Cited

U.S. PATENT DOCUMENTS

P.P. 8,274 6/1993 Jacobsen ..... Plt./86.3

*Primary Examiner*—James R. Feyrer

*Attorney, Agent, or Firm*—Foley & Lardner

[57] ABSTRACT

A distinct cultivar of poinsettia plant named Beckmanns Altrosa, characterized by the combined traits of salmon pink bract color, medium tall and well branched plant habit, medium green foliage, medium early flowering response, and good stability of bract color upon maturation.

1 Drawing Sheet

The present invention relates to a new and distinct cultivar of poinsettia plant, botanically known as *Euphorbia pulcherrima*, and known by the cultivar name Beckmanns Altrosa.

The new cultivar is a naturally occurring mutation of Peterstar, disclosed in U.S. Plant Pat. No. 8,259 and characterized by its bright red bract color, medium green foliage, comparatively compact plant habit, medium early response in autumn, and good branching ability.

The new cultivar was discovered by the inventor Karl-Rudolf Beckmann as a mutation among a group of stock plants of the parent cultivar Peterstar growing in a grenhouse in Goennebeck, Germany in 1991. One branch of the plant displayed bracts having a pink color, compared to the bright red bract color of the parent. Shoots developing from the mutated branch were severed by the inventor, planted as cuttings, and grown out. The mutation was multiplied asexually by the inventor in Goennebeck, Germany and carefully monitored to assess stability. The cloned progeny were found to be stable and substantially identical to the new mutation in all distinguishing characteristics.

Horticultural examination initiated in 1992 and continuing thereafter has demonstrated that the combination of characteristics as herein disclosed for Beckmanns Altrosa are firmly fixed and are retained through successive generations of asexual reproduction.

The following traits have been repeatedly observed and are determined to be basic characteristics of Beckmanss Altrosa which in combination distinguish this poinsettia as a new and distinct cultivar:

1. Uniform salmon pink bract color.
2. Elliptically shaped bracts with somewhat rugose texture.
3. Medium tall, well branched plant habit.
4. Medium green foliage, broad elliptically shaped.
5. Medium early flowering response.
6. Good stability of bract color upon maturation.

Beckmanns Altrosa has not been observed under all possible environmental conditions. The phenotype may vary significantly with variations in environment such as temperature, light intensity, and daylength without, however, any variance in genotype. The following observations, measurements and comparisons describe plants grown in Hillscheid, Germany, under greenhouse conditions which approximate those generally used in commercial practice.

Of the many commercial cultivars known to the inventor, the most similar in comparison to Beckmanns Altrosa in the parent cultivar Peterstar. Beckmanns Altrosa has a uniform salmon pink bract color, compared to the bright red bract color of Peterstar. In addition, the new cultivar has a more compact growth habit which does not require the use of growth regulations, and the finishing time for plants of Beckmanns Altrosa is 4–5 days shorter than for Peterstar.

When compared to Pegirl, disclosed in U.S. Plant Pat. No. 8,274, Beckmann's Altrosa grows less vigorously and its bracts color comparatively earlier. In addition, Beckmann's Altrosa has a more intense pink color (50B) with a slight salmon cast, while the bracts on Pegirl are a brighter pink (51B-C) in color.

The accompanying color photographic drawing shows typical inflorescence and foliage of a potted plant of Beckmanns Altrosa, with colors being as true as possible with illustrations of this type.

In the following description, color references are made to The Royal Horticultural Society Colour Chart. The color values were determined indoors in a north light. The plants described were grown in Hillscheid, Germany (latitude 50°N). They were planted as rooted cuttings in early June, potted in in late June and pinched 14 days later. Plants were grown under dark cloth (short day treatment) from July 25. These plants and those of the comparison cultivar Peterstar were treated with growth regulator Cyocel three times. The last treatment was six weeks before the observation date. Observations and measurements were taken at the beginning of flowering in mid-September.

Classification:

*Botanical.*—*Euphorbia pulcherrima.*

*Commercial.*—Poinsettia, cv. Beckmanns Altrosa.

Parentage: A naturally occurring mutation from the cultivar Peterstar.

Plant Description:

*Form.*—Broad, bushy, 5–6 branches.

*Growth habit.*—Medium growth habit; height approximately 23 cm.

*Rooting.*—Fast; less than 20 days.

*Blooming season.*—From late November (about 8–9 weeks of response time).

*Blooming habit.*—Saleable from late November, when 3–6 bracts are completely colored.

*Foliage.*— Size: Leaf is approximately 13–14 cm in length; petiole is 6 cm in length. Internodes: 20–25 mm. Color: Mature Foliage: Upper surface 137A; under surface 137C. Leaf Petiole: Light red. Shape: Broad, elliptical with weak lobes, rounded base. Texture: Upper side, slightly rugose; lower side, weak veins. Edge of margin: Entire. Disease resistance: The new cultivar has not been observed to have a higher tolerance or a higher susceptibility to diseases or pests than average.

Flowering Description:

*Cyathias.*— Borne: In a narrow cluster. Quantity: 10–15. Retention: Good.

*Bracts.*—Elliptical, folded along the midrib and slightly reflexed, surface rugose; largest colored bract with petiole is 17 cm long.

*Color (Mature bracts in the middle of the involucre).*—Upper surface 50B; lower surface 47D. By comparison, the upper surface of the bracts of Peterstar are bright red 45B. Bract petioles and the base of the midrib are approximately 47A-B in color, but the small veins extending from the midrib are similar in color to the lamina.

Reproductive Organs:

*Glands, nectar cups.*—Orange-yellow.

*Stamens.*—Light red turning to brown, hardly any fertile stamens.

*Pollen.*—Very little, yellow in color.

*Styles.*—White style, 6-lobed light red stigma.

*Ovaries.*—Triangular, 3-celled, 3 ovules.

I claim:

1. A new and distinct poinsettia plant named Beckmanns Altrosa, as illustrated and described.

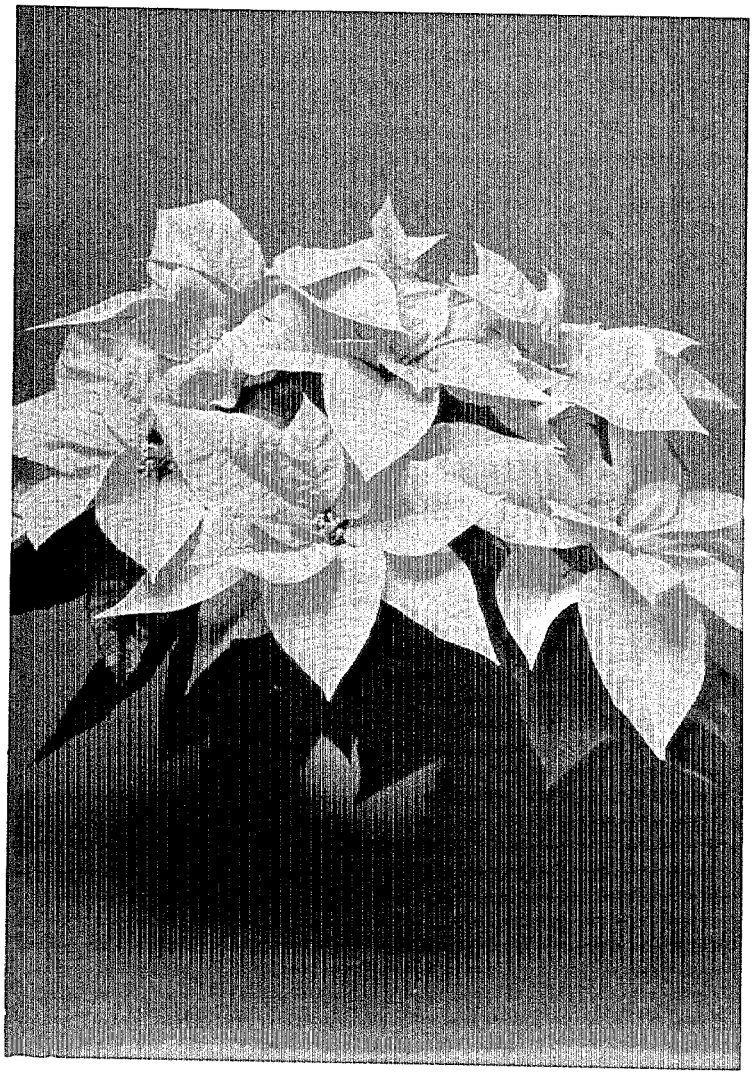

* * * * *